United States Patent [19]

Ishikawa

[11] 4,061,143

[45] Dec. 6, 1977

[54] MEDICAL ADMINISTERING NEEDLE ASSEMBLY WITH FILTER MEANS

[76] Inventor: Soji Ishikawa, No. 8-5, 1-chome, Kamata, Setagaya, Tokyo, Japan

[21] Appl. No.: 694,794

[22] Filed: June 10, 1976

[51] Int. Cl.² ............................................. A61M 5/32
[52] U.S. Cl. ............................... 128/218 N; 128/221
[58] Field of Search ....... 128/218 R, 218 N, 218 NV, 128/218 M, 220, 221, 215, 216, 214 R, 214 F, 214 C, 2 F

[56] References Cited

U.S. PATENT DOCUMENTS

| | | | |
|---|---|---|---|
| 2,833,281 | 5/1958 | Krug | 128/221 |
| 2,857,913 | 10/1958 | Miskel | 128/221 |
| 3,468,308 | 9/1969 | Bierman | 128/214 F |
| 3,757,780 | 9/1973 | Ishikawa | 128/218 N |
| 3,859,999 | 1/1975 | Ishikawa | 128/218 N |

Primary Examiner—John D. Yasko

[57] ABSTRACT

A medical administering needle assembly comprising a generally tubular body portion having an annular end wall formed with projections slightly protruding into the fluid conducting passageway in the body portion and two filter elements having different densities and spaced apart from the annular end wall by means of the projections.

9 Claims, 2 Drawing Figures

MEDICAL ADMINISTERING NEEDLE ASSEMBLY WITH FILTER MEANS

FIELD OF THE INVENTION

The present invention relates to medical administering injectors such as hypodermic, intramuscular or intravenous syringes and dripsets for injecting medical solutions or blood into the bloodstream or body tissues and, more particularly, to a needle assembly constituting such a syringe or for use in an intravenous dripset.

BACKGROUND

When in handling syringes or dripsets for medical administering purposes or during production or transit of such devices, there are a variety of possibilities that solid impurities can be admitted into the syringes or dripsets or admixed to the medical solution or blood which has been introduced into or stored in the devices. These impurities include not only dust or fine particles which have ingressed into the syringe or dripset from external sources but fine fragments of glass or rubber which are produced when an ampoule or other breakable container of a medical solution is opened or during the process in which a rubber plug is fitted on the fluid reservoir or a fluid conducting tube of a dripset prior to administration. The impurities thus present in a medical solution in a syringe or a dripset find their way through the needle holder and the needle into the bloodstream or body tissues of the human body and may injure the vascular tissues.

Medical administering injectors having filter media have therefore been proposed and put into use for the purpose of removing impurities from the medical solution or blood for intravenous transfusion before the solution or blood is discharged from the injection needles or cannulae of the administering devices. The filter medium is ordinarily located within the needle holder of a syringe or of the needle assembly of a dripset for collecting impurities from the medical solution or blood for transfusion at the substantial terminal end of the flow of the fluid through the needle assembly. In some cases, the filter media are located within the barrel of syringes or of adapters of dripsets for collecting impurities before the solution or blood is allowed into the needle holders.

Impurities contained in medical solutions of blood to be dealt by medical administering injectors in general usually range in respect of particle size from the order of microns to the order of hundreds of microns, as is well known in the art. For the purpose that impurities with particle sizes of the order of microns be collected by a filter medium satisfactorily, the filter medium must have voids that measure tenths of microns in diameter or width. If a filter medium having such a density is formed to the thickness required to provide a desired filtering ability and is incorporated in a needle assembly, the flow of the fluid to be passed through the filter medium is subjected to a resistance of a considerable degree and forces the filter medium to move forward in the needle assembly. In the process of injection, the filter medium is thus finally forced against the annular wall at the formost end of the chamber or passageway within which the filter medium is located. When this occurs, the filter medium has its circumferential annular portion covered by the inner face of the annular wall of the needle holder or the barrel of the needle assembly and is allowed to be effective to function as the filter medium only through its central portion coextensive with the cross sectional area of the inlet end of the passageway extending forward from the inner end face of the annular wall which is integral with a tip portion carrying the injection needle (if the filter medium is mounted in the needle holder) or with a tip portion connected to the needle holder (if the filter medium is located within the barrel of the needle assembly). The filter medium in this condition is permitted to exhibit only part of its potential ability and invites deterioration in the collection efficiency. In the case of a dripset, this may cause a failure of the dripset to feed the medical solution into the vein at a desired rate.

Another problem encountered by a filter medium for use in a medical administering injector is that the smaller the voids in the filter medium, the earlier the voids become clogged with solid particles collected by the filter medium. This also gives rise to reduction in the collection efficiency of the filter medium in the process of administration.

SUMMARY OF THE INVENTION

The present invention contemplates elimination of the above described drawbacks inherent in prior-art medical administering needle assemblies.

It is, accordingly, a prime object of the present invention to provide a medical administering needle assembly provided with filter means capable of collecting impurities with particle sizes or the order of microns at an efficiency which is substantially unchanged throughout the administering process.

In accordance with the present invention, such an object is accomplished basically by a medical administering needle assembly having longitudinally aligned foremost and rearmost ends as regards the direction in which a fluid is to be forced to flow through the assembly when the assembly is in use, comprising a generally tubular body portion which is formed with a longitudinal passageway having an axis therethrough and open at the rearmost end of the end faces and which has a front end wall formed with an opening at the foremost end of the passageway, the front end wall having at the foremost end of the passageway an annular inner face having an outer circumferential end at the foremost end of the passageway an annular inner face having an outer circumferential end at the foremost end of the inner peripheral surface of the body portion and an inner circumferential end circumscribing the rearmost end of the aforesaid opening, the end wall of the body portion being further formed with a plurality of projections protruding rearwardly from the inner face of the end wall and spaced apart from each other about the axis of the passageway in the body portion, the projections having respective rear end faces located in a common plane substantially perpendicular to the axis of the passageway in the body portion; a tip portion forwardly projecting from the front end wall of a tip portion forwardly projecting from the front end wall of the body portion and formed with a longitudinal passageway rearwardly merging with the opening in the end wall portion and communicating with the passageway in the body portion through the opening; a first disc-shaped filter element located within the passageway in the body portion and having a front end face in contact with the rear end faces of said projections; and a second disc-shaped filter element located within the passageway in the body portion rearwardly of the first filter element and having a front end face in contact over substantially its entire area with the rear end face of the first filter element, each of the first and second filter elements having its outer peripheral surface closely received on the inner peripheral surface of the body portion and being formed with a each of the first and second filter elements having a multiplicity of voids, the first filter element being denser than the second filter element and the voids in the first filter element being smaller than the voids in the second filter element. Preferably, the voids in the first filter element have sizes smaller than 1 micron and the voids in the second filter element have sizes larger than 1 micron and smaller than 10 microns. The first filter element of such a nature may be constructed by an ultrafilter or a membrane filter having a thickness smaller than 0.8 mm and larger than 0.1 mm. On the other hand, the second filter element may be constructed of a fiber mat having a thickness larger than 0.8 mm. The aforesaid projections formed on the end wall of the body portion are preferably located substantially symmetrically about the center axis of the opening in the end wall. In this instance, the longitudinal passageway in the body portion preferably has a center axis substantially in line with the center axis of the opening in the end wall. The body portion and the tip portion of the needle assembly thus arranged may constitute either the needle holder having the tip portion connected to an injection needle or the barrel having the tip portion adapted to be engaged by the needle holder.

BRIEF DESCRIPTION OF THE DRAWING

The features of the needle assembly according to the present invention will be understood more clearly from the following description taken in conjunction with the accompanying drawing, in which.

DETAILED DESCRIPTION

Figure 1:
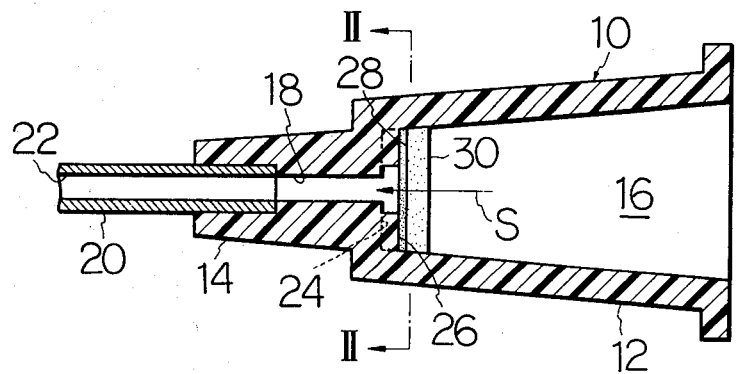
FIG. 1 is a longitudinal sectional view of a sole preferred embodiment of the present invention.
Figure 2:
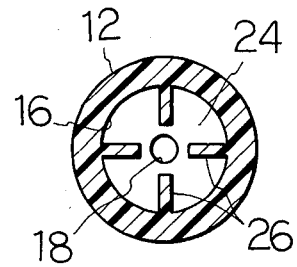
FIG. 2 is a cross sectional view taken on line II-II of FIG. 1.

Referring to FIGS. 1 and 2 of the drawing, the present invention is shown embodied in a needle holder 10 to form part of a medical administering syringe. The needle holder 10 has longitudinally aligned foremost and rearmost ends in terms of the direction, indicated by arrow S, in which a fluid is to be forced to flow when the needle assembly is put to use. The needle holder 10 comprises a generally tubular body portion 12 and a tip portion 14 and is formed with a longitudinal passageway 16 in the body portion 12 and a longitudinal passageway 18 in the tip portion 14. The tip portion 14 is fixedly connected to an injection needle 20, only a rear end portion of which is illustrated in FIG. 1. The injection needle 20 is formed with an elongated passageway 22 extending throughout the length of the needle 20 and in communication with the passageway 18 in the tip portion 14. Though not shown, the injection needle 20 has a pointed open foremost end as is well known. The body portion 12 and the tip portion 14 are shown to be slightly tapered toward their respective foremost ends but, if desired, one or each of the portions may have a generally cylindrical configuration.

The body portion 12 is open at its rearmost end and has an annular wall 24 at the opposite end of the passageway 16. The annular end wall 24 is formed with a central opening through which the passageway 16 in the body portion 12 is in communication with the passageway 16 in the tip portion 14 and accordingly with the passageway 22 in the injection needle 20. The passageway 16 in the body portion 12, the opening in the end wall 24, the passageway 18 in the tip portion 14 and the passageway 22 in the needle 20 are assumed to have respective center axes aligned with each other and provide a conducting path for the stream of fluid to be passed therethrough as indicated by arrow S. The body and tip portions 12 and 14 thus integral with each other through the end wall 24 of the body portion 12 are preferably formed of a rigid plastic while the injection needle 20 is usually formed of stainless steel.

The central opening in the end wall 24 of the body portion 12 is smaller in cross sectional area than the passageway 16 in the body portion 12 so that the end wall 24 has an annular inner face located at the foremost end of the passageway 16 and having an outer circumferential end at the foremost end of the inner peripheral surface of the body portion 12 and an inner circumferential end circumscribing the rearmost end of the opening in the end wall 24. The end wall 24 is further formed with a plurality of projections 26 which protrude rearwardly from the above mentioned annular inner face of the end wall 24 and which are spaced apart, preferably equiangularly from one another, about the center axis of the passageway 16 in the body portion 12. The projections 26 have respective rear end faces located on a common plane substantially perpendicular to the center axis of the passageway 16 in the body. As better seen in FIG. 2, the projections 26 are, in the embodiment herein shown, four in number and are arranged substantially in symmetrically about the center axis of the passageway 1b in the body portion 12.

The needle holder 10 thus constructed has mounted therein first and second disc shaped filter elements 28 and 30 which are located within the passageway 16 in the body portion 12 and which have their respective circumferential ends closely received on the inner peripheral surface of the body portion 12. The first filter element 28 has one (the front) end face in contact with the projections 26 of the end wall 24 and the second filter element 30 has one (the front) end face in contact with the other (rear) end face of the first filter element 28. The first filter element 28 is assumed to be constructed by an ultrafilter or a membrane filter having the thickness less than 0.8 mm and formed with a multiplicity of voids having the sizes smaller than 1 micron. On the other hand, the second filter element 30 is assumed to be constructed of a fiber mat having a thickness greater than 0.8 mm and formed with a multiplicity of voids having sizes larger than 1 micron and smaller than 10 microns. In this instance, the term "sizes" of the voids may be the diameters of the micropores in the ultrafilter constituting the first filter element 28 or the diameters, lengths and/or widths of the pores, meshes and/or interstices between the individual fibers or filaments of the fiber mat constituting the second filter element 30.

With the first and second filter elements 28 and 30 thus arranged in the needle holder 10, the stream of fluid, such as liquid medicament or blood for intravenous transfusion, entering the passageway 16 in the body portion 12 forwardly through the rearmost end of the needle holder 12 is first passed through the second filter element 30 and is cleared of particles having relatively large sizes. The stream of the fluid is then passed through the first filter element 28 denser than the second filter element 30 and is cleared of relatively small particles by the ultrafilter constituting the first filter element 28. The impurities initially contained in the fluid passed into the needle holder 10 are, thus, collected in two consecutive steps by the first and second filter elements 28 and 30 and, because of the fact that the stream of the fluid entering the first filter element 28 has been cleared of the relatively large-sized particles by the second filter element 30, the possibility of the first filter element 28 becoming clogged by impurities is greatly reduced. Because, furthermore, the first filter element 28 is spaced rearwardly from the inner face of the annular end wall 24 of the body portion 12 by the projections 26, the first filter element 28 is operable substantially throughout its area except for its areas contacting the projections 26. The filter elements 28 and 30 are thus permitted to exhibit their original filtering efficiencies throughout the administering process.

The features of the present invention are advantageous especially when incorporated into needle assemblies of the disposable type but may be applied to needle assemblies of the type adapted for repeated use if the filter elements are arranged to be replaceable with new ones each time the needle assembly is used.

What is claimed is:

1. A medical administering needle assembly having longitudinally aligned foremost and rearmost ends as regards the direction in which a fluid is to be forced to flow through the assembly when the assembly is in use, comprising:

a generally tubular body portion which is formed with a longitudinal passageway having an axis therethrough and open at the rearmost end of the body portion and which has a front end wall formed with an opening at the foremost end of the passageway, the front end wall having at the foremost end of the passageway an annular inner face having an outer circumferential end at the foremost end of the inner peripheral surface of the body portion and an inner circumferential end circumscribing the rearmost end of said opening, said end wall being further formed with a plurality of projections protruding rearwardly from said annular inner face and spaced apart from each another about said axis of the passageway in the body portion, said projections having respective rear end faces in a common plane substantially perpendicular to said axis;

a tip portion forwardly projecting from said front end wall and formed with a longitudinal passageway rearwardly merging with said opening and communicating with the passageway in the body portion through the opening;

a first disc-shaped filter element located within the passageway in the body portion and having a front end face in contact with said rear end faces of said projections; and a second disc-shaped filter element located within the passageway in said body portion rearwardly of said first filter element and having a front end face in contact over substantially its entire area with the rear end face of said first filter element, each of the first and second filter elements having its outer peripheral surface closely received on the inner peripheral surface of said body portion and being formed with a multiplicity of voids, the first filter element being denser than the second filter element and the voids in the first filter element being smaller in size than the voids in the second filter element.

2. A medical administering needle assembly as set forth in claim 1, in which the voids in said first filter element have sizes smaller than 1 micron and the voids in said second filter element have sizes larger than 1 micron and smaller than 10 microns.

3. A medical administering needle assembly as set forth in claim 2, in which said first filter element is constructed by an ultrafilter having a thickness smaller than 0.8 millimeter and said second filter element is constructed of a fiber mat having a thickness larger than 0.8 millimeter.

4. A medical administering needle assembly as set forth in claim 1, in which said projections are located substantially in symmetry about the center axis of said opening in said end wall.

5. A medical administering needle assembly as set forth in claim 1, in which said body portion and said tip portion constitute a needle holder having the tip portion connected to an injection needle.

6. A medical administering needle assembly as set forth in claim 1, in which said body portion and said tip portion constitute a barrel of a syringe having the tip portion adapted to be engaged by a needle holder.

7. A medical administering needle assembly as set forth in claim 1, in which said projections are spaced apart from each other circumferentially in the passageway in the body portion.

8. A medical administering needle assembly as set forth in claim 7, in which said projections are spaced apart from each other circumferentially in the passageway in the body portion.

9. A medical administering needle assembly as set forth in claim 8, in which said projections are substantially regularly spaced apart from each other circumferentially about said axis of the passageway in the body portion.

* * * * *